(12) United States Patent
Alexandroni et al.

(10) Patent No.: US 11,950,951 B2
(45) Date of Patent: Apr. 9, 2024

(54) SYSTEMS AND METHODS FOR C-ARM FLUOROSCOPE CAMERA POSE REFINEMENT WITH SECONDARY MOVEMENT COMPENSATION

(71) Applicant: Covidien LP, Mansfield, MA (US)

(72) Inventors: Guy Alexandroni, Yehud-Monosson (IL); Ariel Birenbaum, Raanana (IL)

(73) Assignee: Covidien LP, Mansfield, MA (US)

( * ) Notice: Subject to any disclaimer, the term of this patent is extended or adjusted under 35 U.S.C. 154(b) by 262 days.

(21) Appl. No.: 17/575,465

(22) Filed: Jan. 13, 2022

(65) Prior Publication Data

US 2022/0240886 A1 Aug. 4, 2022

Related U.S. Application Data

(60) Provisional application No. 63/143,586, filed on Jan. 29, 2021.

(51) Int. Cl.
*A61B 6/00* (2006.01)
*A61B 90/00* (2016.01)

(52) U.S. Cl.
CPC ............ *A61B 6/547* (2013.01); *A61B 6/4441* (2013.01); *A61B 6/487* (2013.01); *A61B 90/39* (2016.02); *A61B 2090/3966* (2016.02)

(58) Field of Classification Search
CPC .. A61B 6/487; A61B 2090/3966; A61B 90/39
See application file for complete search history.

(56) References Cited

U.S. PATENT DOCUMENTS

| | | | |
|---|---|---|---|
| 6,373,916 B1 | 4/2002 | Inoue et al. | |
| 6,473,634 B1 | 10/2002 | Barni | |
| 7,065,393 B2 | 6/2006 | Sati et al. | |
| 7,551,759 B2 | 6/2009 | Hristov et al. | |
| (Continued) | | | |

FOREIGN PATENT DOCUMENTS

| | | |
|---|---|---|
| DE | 102010034678 | 9/2018 |
| WO | 2008140486 A2 | 11/2008 |

OTHER PUBLICATIONS

PCT Search Report and Written Opinion issued in PCT Application No. PCT/US2022/014219 dated May 19, 2022.

*Primary Examiner* — Dani Fox
(74) *Attorney, Agent, or Firm* — Weber Rosselli & Cannon LLP

(57) ABSTRACT

Imaging systems and methods compensate for wigwag movement of a C-arm fluoroscope to refine camera pose estimates. The methods involve computing a primary movement axis from samples of markers in fluoroscopic images of a fluoroscopic sweep of a structure of markers and processing the primary movement axis to obtain a secondary movement axis. The methods further involve aligning two-dimensional samples of each marker with the primary and secondary movement axes to obtain an aligned signal and determining a difference signal for a secondary component of the aligned signal. The difference signal is then converted to a rotation axis translation signal. The method further involves estimating a 3D position of the rotation axis. The estimated pose of the C-arm fluoroscope is then refined to compensate for the wigwag movement using the rotation axis translation signal and the estimated 3D position of the rotation axis.

19 Claims, 11 Drawing Sheets

(56) References Cited

U.S. PATENT DOCUMENTS

| | | |
|---|---|---|
| 7,916,918 B2 | 3/2011 | Suri et al. |
| 8,159,543 B2 | 4/2012 | Drouot |
| 8,482,606 B2 | 7/2013 | Razzaque et al. |
| 8,625,869 B2 | 1/2014 | Harder et al. |
| 9,398,675 B2 | 7/2016 | Eaves |
| 9,433,390 B2 | 9/2016 | Nathaniel et al. |
| 9,833,167 B2 | 12/2017 | Cohen et al. |
| 10,084,962 B2 | 9/2018 | Kokaram et al. |
| 10,127,629 B2 | 11/2018 | Razzaque et al. |
| 10,130,316 B2 | 11/2018 | Funabasama et al. |
| 10,172,585 B2 | 1/2019 | Amiri |
| 10,426,559 B2 | 10/2019 | Graetzel et al. |
| 10,674,970 B2 | 6/2020 | Averbuch et al. |
| 10,799,298 B2 | 10/2020 | Crawford et al. |
| 10,896,506 B2 | 1/2021 | Zhao et al. |
| 2002/0085681 A1 | 7/2002 | Jensen |
| 2003/0130576 A1* | 7/2003 | Seeley .................. A61B 90/36 600/426 |
| 2003/0219102 A1 | 11/2003 | Mitschke et al. |

* cited by examiner

SYSTEMS AND METHODS FOR C-ARM FLUOROSCOPE CAMERA POSE REFINEMENT WITH SECONDARY MOVEMENT COMPENSATION

FIELD

This disclosure relates to the field of imaging, and particularly to secondary movement compensation and C-arm fluoroscope camera pose refinement.

BACKGROUND

A fluoroscopic imaging device is commonly located in the operating room during procedures to navigate a medical device to a target within a patient's body. The fluoroscopic imaging device may be used by a clinician, for example, to visualize and confirm the placement of a medical device while it is being navigated to a desired location or after it has been navigated to a desired location. Although standard fluoroscopic images display highly dense objects such as metal tools and bones as well as large soft-tissue objects such as the heart, the fluoroscopic images have difficulty resolving small soft-tissue objects of interest, such as lesions, which are to be ablated. Furthermore, the fluoroscope image is only a two-dimensional projection, while 3D imaging is needed for accurately and safely navigating within the body.

Therefore, a fast, accurate, and robust three-dimensional reconstruction of structures based on fluoroscopic imaging performed during medical procedures is needed.

SUMMARY

In one general aspect, this disclosure features a method of compensating for secondary movement of a C-arm fluoroscope. The method includes receiving fluoroscopic images obtained from a fluoroscopic sweep by the C-arm fluoroscope and detecting markers of a structure of two-dimensional (2D) markers in the fluoroscopic images to obtain detected markers. The method further includes determining movement of the markers based on the detected markers. The method further includes estimating a primary movement axis based on the movement of the markers and determining a secondary movement axis based on the primary movement axis. The method further includes estimating a translation of the markers in a direction of the secondary movement axis and estimating a rotation axis translation based the translation of the markers. The method further includes estimating a three-dimensional (3D) position of a rotation axis, estimating poses for the fluoroscopic images, and refining the poses for the fluoroscopic images based on the rotation axis translation and the 3D position of the rotation axis.

In aspects, implementations of this disclosure may include one or more of the following features. Each marker of the structure of markers may be a radiopaque bead or a radiopaque marker. The structure may be a two-dimensional (2D) grid pattern.

In aspects, estimating a translation of the markers may include aligning each marker with the primary movement axis and the secondary movement axis to obtain an aligned signal, and determining a difference signal of each marker for a secondary component of the aligned signal.

In aspects, the secondary movement axis is determined by processing the determined primary movement axis with a Graham-Schmidt algorithm.

In aspects, estimating the 3D position of the rotation axis may include fitting a plane to the main camera axes of the C-arm fluoroscope over the fluoroscopic sweep, and computing an axis normal to the plane to obtain the 3D position of the rotation axis.

In aspects, estimating the primary movement axis of the markers includes determining, for each of the markers, difference vectors between pairs of detected markers in adjacent pairs of frames of the fluoroscopic images, and computing, for each pair of frames, a weighted average of the difference vectors. The weights applied to the difference vectors may be distances between the pairs of detected markers.

In aspects, estimating the primary movement axis of a marker may further include computing a dot product between difference vectors, determining that the dot product is less than a threshold, and in response to determining that the dot product is less than the threshold, setting the weights of the difference vectors to zero. Estimating the primary movement axis of a marker may further include recomputing, for each pair of frames, a weighted average of the difference vectors, determining that weights of a current iteration are the same as weights of a previous iteration, and in response to determining that the weights of a current iteration are the same as the weights of a previous iteration, stopping computing of the weighted average.

In another general aspect, this disclosure features a method for estimating wigwag movement in a C-arm fluoroscope. The method includes receiving fluoroscopic images from a sweep of a C-arm fluoroscope and obtaining two-dimensional (2D) samples of each marker from the fluoroscopic images. The method further includes estimating a main movement axis of each marker based on the 2D samples of each marker and determining a secondary movement axis of each marker based on the main movement axis of each marker. The method further includes aligning 2D samples of each marker with the main movement axis and the secondary axis for each marker to obtain an aligned signal of each marker. The method further includes determining a velocity signal of each marker for a secondary component of the aligned signal of each marker, converting the velocity signals of the markers to a rotation axis translation signal, and estimating a rotation axis for the rotation axis translation signal.

In aspects, implementations of this disclosure may include one or more of the following features. Each marker may be part of a structure of markers. The structure may be a two-dimensional (2D) grid pattern.

In aspects, estimating the rotation axis may include fitting a plane to the main camera axes of the C-arm fluoroscope over the sweep and computing a normal axis to the plane to obtain the rotation axis.

In aspects, converting the velocity signals of the markers to a rotation axis translation signal may include averaging the velocity signals for all markers for each of the fluoroscopic images to obtain an averaged velocity signal, and converting the averaged velocity signal to the rotation axis translation signal. Converting the averaged velocity signal to the rotation axis translation signal may include integrating the averaged velocity signal across all fluoroscopic images to obtain the rotation axis translation signal.

In aspects, estimating the main movement axis of each marker of the structure of markers may include determining, for each marker of the structure of markers, difference vectors between pairs of markers in adjacent pairs of frames of the fluoroscopic images, and computing, for each pair of frames, a weighted average of the difference vectors. The weights applied to the difference vectors may be distances between the pairs of markers.

In aspects, the secondary movement axis is determined by processing the determined main movement axis of each marker of the structure of markers with a Graham Schmidt algorithm.

In aspects, converting the velocity signal of each marker to a rotation axis velocity signal may include determining a similarity ratio for each marker and applying the similarity ratio to each marker to obtain the rotation axis velocity signal.

In aspects, the method may further include estimating a pose for each of the fluoroscopic images based on the 2D samples of the markers, the rotation axis translation signal, and the rotation axis.

In aspects, the markers may be a grid of radiopaque beads.

BRIEF DESCRIPTION OF THE DRAWINGS

Various exemplary aspects are illustrated in the accompanying figures with the intent that these examples are not restrictive. It will be appreciated that for simplicity and clarity of the illustration, elements shown in the figures referenced below are not necessarily drawn to scale. Also, where considered appropriate, reference numerals may be repeated among the figures to indicate like, corresponding or analogous elements. The figures are listed below.

DETAILED DESCRIPTION

In an ENB platform, a C-arm fluoroscope is used to generate intra-operative 3D imaging of the target and medical device area, allowing local correction to registration. The mechanical assemblies attached to the horizontal cross-arm of the C-arm fluoroscope can move back and forth along the rotation axis of the C-arm fluoroscope. This movement is also referred to as "wigwag" movement. The C-arm fluoroscope may also include a wigwag brake. The wigwag brake may be released by placing the brake handle in an unlocked position. This allows a clinician to move the horizontal cross-arm, C-arm, and L-arm into position for performing a fluoroscopic sweep. Once the horizontal cross-arm, C-arm, and L-arm are in the desired position, the wigwag brake is locked by placing the brake handle in the locked position. As a C-arm fluoroscope wears out, the wigwag lock may loosen. As a result, during a fluoroscopic sweep, there may be slight movement perpendicular to the sweeping direction.

Because of this degree of freedom in the C-arm geometry, the camera solutions generated by the camera pose estimation algorithm may be inaccurate. According to this disclosure, a post processing camera refinement algorithm estimates the wigwag movement in the fluoroscopic video by tracking and analyzing the trajectories of markers on the antenna board. The estimated wigwag movement is then used to refine the camera solutions. The outcome is more accurate registration correction and sharper 3D visualization of the target vicinity.

In any of the C-arm positioning cases, the markers' main movement axis is computed, and the orthogonal axis is computed based on the markers' main movement axis. In order to understand the movement direction of the markers, the markers are tracked. Next, each marker sample is analyzed and the main movement axis and the secondary, orthogonal axis, which contains the wigwag movement, are estimated. The estimated movement axes are used to estimate the markers wigwag translation relative to the average position. The markers wigwag translation in the image plane is used to estimate the rotation axis translation. Then, the temporal 3D position of the rotation axis is used together with the fixed marker positions to refine the pose of the fluoroscope.

Figure 1:
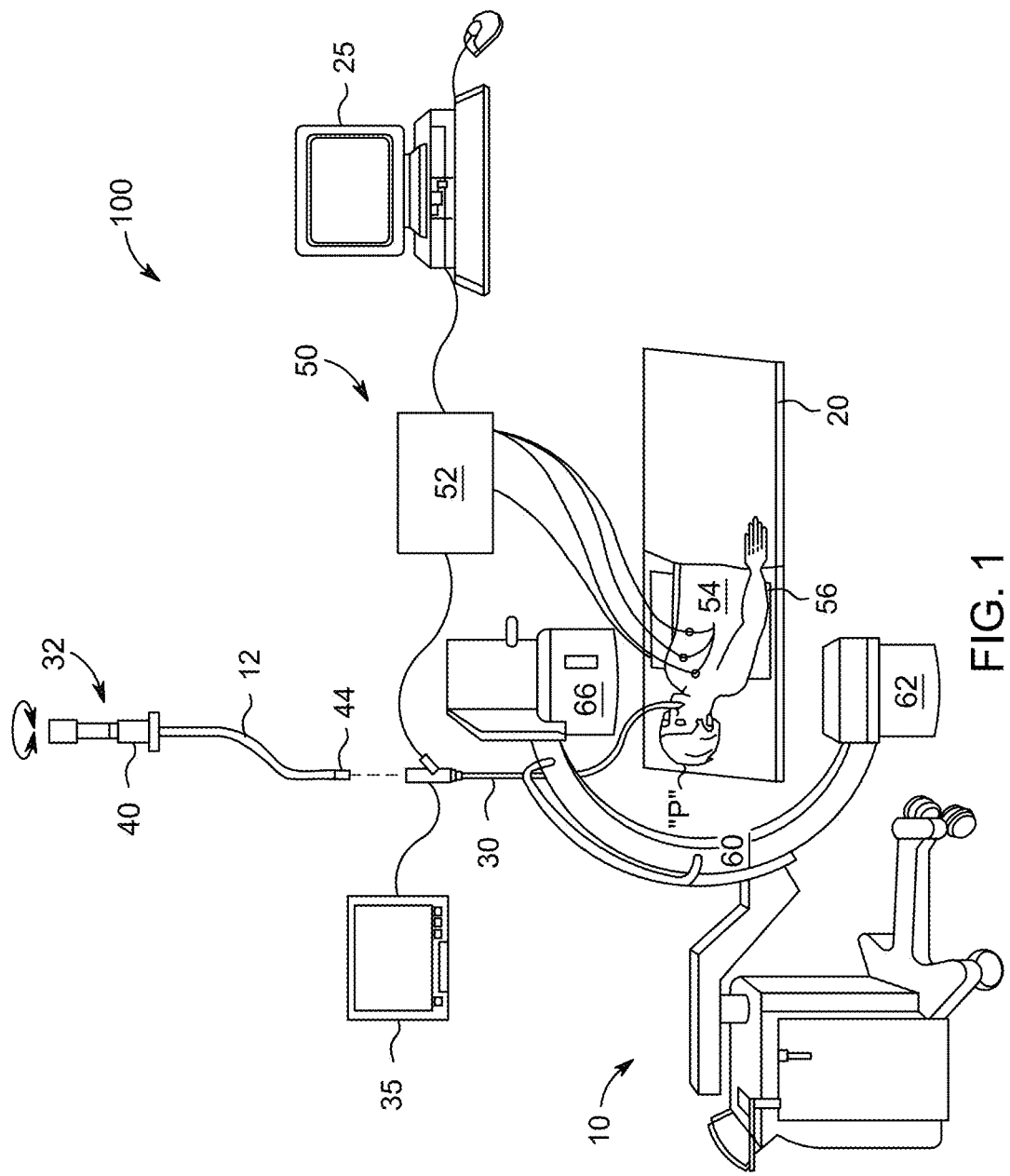
FIG. 1 is a schematic diagram of an exemplary system for constructing fluoroscopic-based three-dimensional volumetric data in accordance with aspects of this disclosure.

FIG. 1 depicts an aspect of a system 100 that may be configured to construct fluoroscopic-based three dimensional volumetric data of a target area including at least a portion of the lungs of a patient from 2D fluoroscopic images. System 100 may be further configured to facilitate advancement of a medical device to the target area by using Electromagnetic Navigation Bronchoscopy (ENB) and for determining the location of a medical device with respect to the target.

The system 100 may be configured for reviewing CT image data to identify one or more targets, planning a pathway to an identified target (planning phase), navigating a catheter 12 of a catheter guide assembly 40 to a target (navigation phase) via a user interface, and confirming placement of the catheter 12 (or any portion of the catheter guide assembly 40 or any instruments inserted therethrough) relative to the target. One such electromagnetic navigation system is the ELECTROMAGNETIC NAVIGATION BRONCHOSCOPY® system currently sold by Medtronic PLC. The target may be tissue of interest, e.g., tissue to be ablated, or a region of interest identified during review of the CT image data during the planning phase. Following navigation, a medical instrument such as a biopsy tool, delivery device, or treatment device may be inserted into the catheter 12 to obtain a tissue sample from the tissue located at, or proximate to, the target, deliver items or therapies to the region, or treat the region.

As shown in FIG. 1, catheter 12 is part of a catheter guide assembly 40 which extends distally from a handle 41 of the catheter guide assembly 40. In practice, the catheter 12 may be inserted into bronchoscope 30 for access to a luminal network of the patient "P." Specifically, catheter 12 of catheter guide assembly 40 may be inserted into a working channel of bronchoscope 30 for navigation through a patient's luminal network. A locatable guide (LG) 32, including a sensor 44 disposed thereon, is inserted into the catheter 12 and locked into position such that the sensor 44 extends a desired distance beyond the distal tip of the catheter 12. The position and orientation of the sensor 44 relative to a reference coordinate system, and thus the distal end of the catheter 12, within an electromagnetic field can be derived. Catheter guide assemblies 40 are currently marketed and sold by Medtronic PLC under the brand names SUPERDIMENSION® Procedure Kits, or EDGE' Procedure Kits, and are contemplated as useable with this disclosure.

Figure 2A:
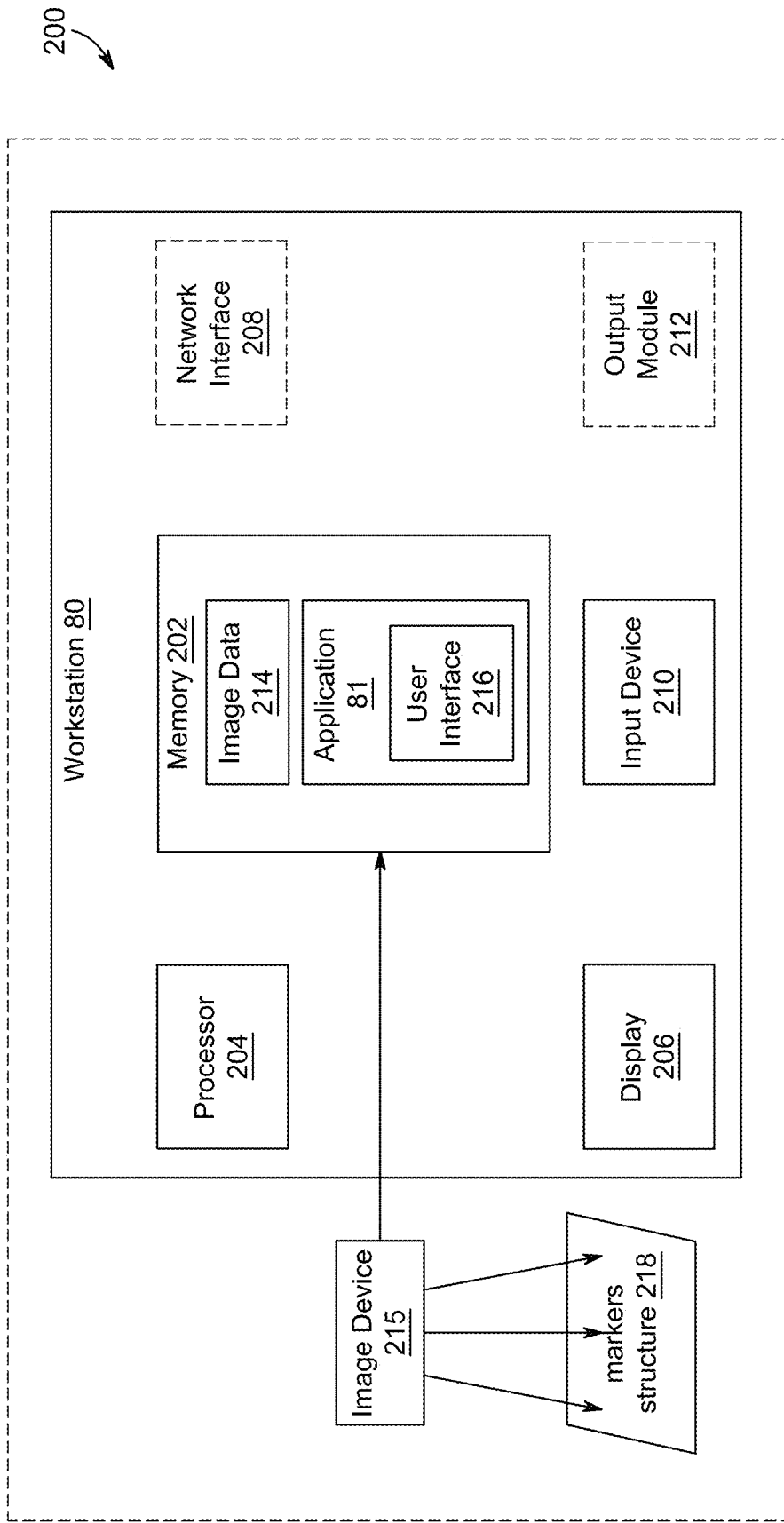
FIG. 2A is a schematic diagram of a system configured for use with aspects of this disclosure.
Figure 2B:
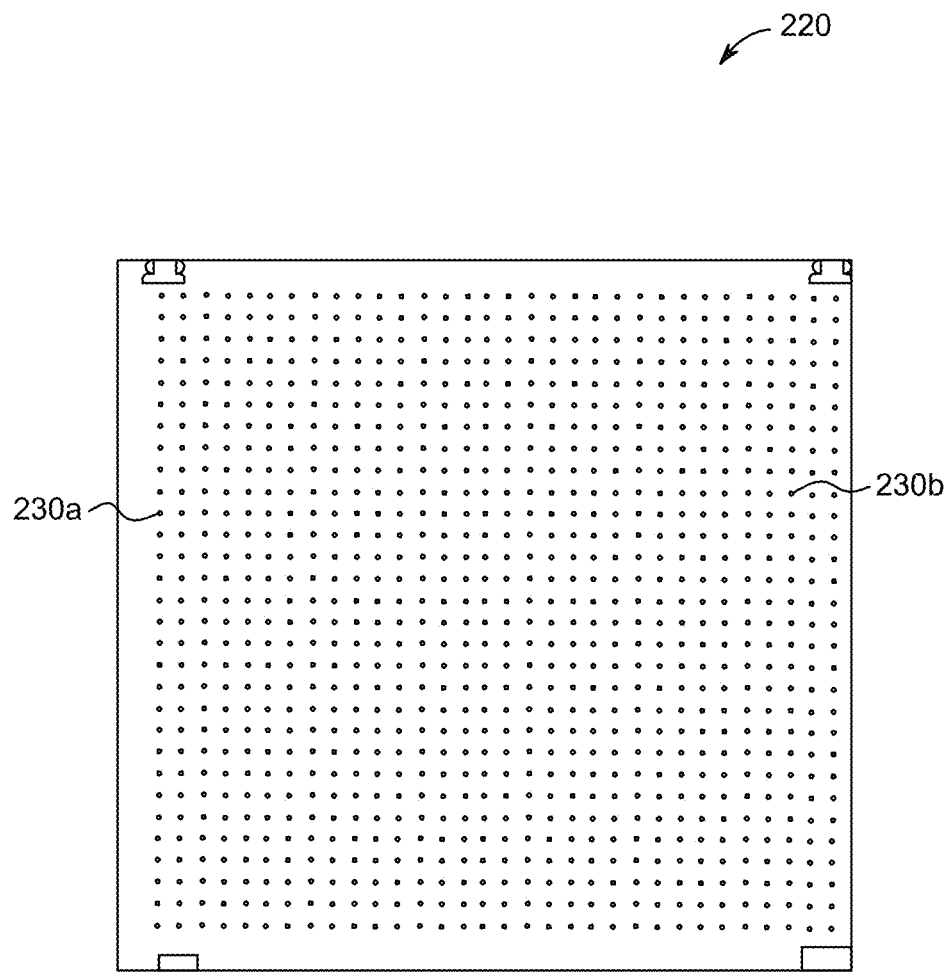
FIG. 2B is a schematic illustration of a two-dimensional grid structure of markers in accordance with one aspect of the disclosure.

EMN system 100 generally includes an operating table 20 configured to support a patient "P"; a bronchoscope 30 configured for insertion through the patient "P's" mouth into the patient "P's" airways; monitoring equipment 35 coupled to bronchoscope 30 (e.g., a video display for displaying video images received from the video imaging system of bronchoscope 30); a tracking system 50 including a tracking module 52, reference sensors 54, and a transmitter mat 56; a structure of markers, e.g., the two-dimensional (2D) grid structure of sphere markers 220 of FIG. 2B, which may be coupled to the transmitter mat 56; and a computing device 25 including software and/or hardware used to facilitate identification of a target, pathway planning to the target, navigation of a medical device or instrument to the target, and confirmation of placement of an catheter 12, or a suitable device therethrough, relative to the target. Computing device 25 may be similar to workstation 80 of FIG. 2A and may be configured, among other functions, to execute the methods of FIGS. 4 and 5.

A fluoroscopic imaging device 10 capable of acquiring fluoroscopic or x-ray images or video of the patient "P" is also included in aspects of system 100. The fluoroscopic images, series of images, or video captured by the fluoroscopic imaging device 10 may be stored within the fluoroscopic imaging device 10 or transmitted to computing device 25 for storage, processing, and display as described in more detail herein. Additionally, the fluoroscopic imaging device 10 may move relative to the patient "P" so that images may be acquired from different angles or perspectives relative to the patient "P" to create a sequence of fluoroscopic images, such as a fluoroscopic video.

The pose of fluoroscopic imaging device 10 relative to patient "P" may be estimated using fluoroscopic images from a fluoroscopic sweep and the structure of markers. The structure of markers is positioned under patient "P," between patient "P" and operating table 20 and between patient "P" and a radiation source of fluoroscopic imaging device 810. The structure of markers may be positioned between patient "P" and operating table 20 near or under the target area within the patient. The structure of markers and the transmitter mat 56 may be two separate elements which are coupled in a fixed manner or alternatively may be manufactured as a single unit. Fluoroscopic imaging device 10 may include a single imaging device or more than one imaging device. In embodiments including multiple imaging devices, each imaging device may be a different type of imaging device or the same type.

Fluoroscopic imaging device 10 may be a C-mount fluoroscope, which includes a C-arm 60. At one end of the C-arm 60 is an X-ray source 62 that includes an X-ray tube and a collimator (not shown). At the other end of the C-arm 60 is an X-ray detector 66 that includes an anti-scatter grid, an image intensifier, and a CCD camera (not shown). The collimator blocks the X-rays emerging from X-ray tube except at an aperture (not shown). A cone of X-rays emerges from the aperture and impinges on the anti-scatter grid and the image intensifier of the X-ray detector 66. The image created in the image intensifier is captured by the CCD camera. Depending on the spatial density distribution in an object such as a patient that is traversed by the cone, each element of the CCD array of the CCD camera receives more or less light from the image intensifier, and the corresponding pixel of the image produced by the C-mount fluoroscope is correspondingly darker or lighter.

Computing device 25 may be any suitable computing device including a processor and storage medium, wherein the processor is capable of executing instructions stored on the storage medium. The computing device 25 is operably coupled to some or all of the components of system 100 including bronchoscope 30, catheter guide assembly 40, locatable guide 32, and tracking system 50. The computing device 25 may include a database configured to store patient data, CT data sets including CT images and volumetric renderings, fluoroscopic data sets including fluoroscopic images and video, navigation plans, and any other such data. Although not explicitly illustrated, the computing device 25 may include inputs, or may otherwise be configured to receive, CT data sets, fluoroscopic images or video, and other data described herein. Additionally, computing device 25 includes a display configured to display graphical user interfaces. Computing device 25 may be connected to one or more networks through which one or more databases may be accessed.

With respect to the planning phase, computing device 25 utilizes previously acquired CT image data for generating and viewing a three-dimensional model of the patient's "P's" airways, enables the identification of a target on the three-dimensional model (automatically, semi-automatically, or manually), and allows for determining a pathway through the patient's "P's" airways to tissue located at and around the target. More specifically, CT images acquired from previous CT scans are processed and assembled into a three-dimensional CT volume, which is then utilized to generate a three-dimensional model of the patient's "P's" airways.

The three-dimensional model may be displayed on a display associated with computing device 25, or in any other suitable fashion. Using computing device 25, various views of the three-dimensional model or two-dimensional images generated from the three-dimensional model are presented. The three-dimensional model may be manipulated to facilitate identification of target on the three-dimensional model or two-dimensional images, and selection of a suitable pathway through the patient's "P's" airways to access tissue located at the target. Once selected, the pathway plan, three-dimensional model, and images derived therefrom, can be saved and exported to a navigation system for use during one or more navigation phases. One such planning software is the ILOGIC® planning suite currently sold by Medtronic PLC.

With respect to the navigation phase, a six degrees-of-freedom electromagnetic tracking system 50 or other suitable positioning measuring system may be utilized for performing registration of the images and the pathway for navigation, although other configurations are also contemplated. Tracking system 50 includes a tracking module 52, a reference sensors 54, and a transmitter mat 56. Tracking system 50 is configured for use with a locatable guide 32 and sensor 44. As described above, locatable guide 32 and sensor 44 are configured for insertion through a catheter 12 into a patient "P's" airways (either with or without bronchoscope 30) and are selectively lockable relative to one another via a locking mechanism.

Transmitter mat 56 is positioned beneath patient "P." Transmitter mat 56 generates an electromagnetic field around at least a portion of the patient "P" within which the position of reference sensors 54 and the sensor 44 can be determined with use of a tracking module 52. The transmitter mat 56 may include a structure or grid of at least partially radiopaque markers, which are used in some aspects of this disclosure to determine the 3D shape of a medical device or catheter being guided towards a target. In some aspects, one or more of reference sensors 54 are attached to the chest of the patient "P" in addition to the transmitter mat 56. In other aspects, only the mat is utilized. The six degrees of freedom coordinates of reference sensors 54 are sent to computing device 25 (which includes the appropriate software) where they are used to calculate a patient coordinate frame of reference.

Registration is generally performed to coordinate locations of the three-dimensional model and two-dimensional images from the planning phase with the patient's "P's" airways as observed through the bronchoscope 30, and allow for the navigation phase to be undertaken with precise knowledge of the location of the sensor 44, even in portions of the airway where the bronchoscope 30 cannot reach. Other suitable registration techniques and their implementation in luminal navigation are also contemplated by this disclosure.

Registration of the patient "P's" location on the transmitter mat 56 is performed by moving locatable guide 32 through the airways of the patient "P." More specifically, data pertaining to locations of sensor 44, while locatable guide 32 is moving through the airways, is recorded using transmitter mat 56, reference sensors 54, and tracking module 52. A shape resulting from this location data is compared to an interior geometry of passages of the three-dimensional (3D) model generated in the planning phase, and a location correlation between the shape and the 3D model based on the comparison is determined, e.g., utilizing the software on computing device 25. Other registration methods are contemplated by this disclosure including, for example, fluoroscopic registration with the 3D model, shape matching, and other suitable techniques for registering operative images of anatomical features to preoperative images of those same anatomical features. In aspects, these other registration methods may or may not utilize the sensor 44 to perform registration.

In addition, the software identifies non-tissue space (e.g., air-filled cavities) in the three-dimensional model. The software aligns, or registers, an image representing a location of sensor 44 with the three-dimensional model and two-dimensional images generated from the three-dimension model, which are based on the recorded location data and an assumption that locatable guide 32 remains located in non-tissue space in the patient "P's" airways. Alternatively, a manual registration technique may be employed by navigating the bronchoscope 30 with the sensor 44 to pre-specified locations in the lungs of the patient "P", and manually correlating the images from the bronchoscope to the model data of the three-dimensional model.

Following registration of the patient "P" to the image data and pathway plan, a user interface is displayed in the navigation software of system 100 which sets for the pathway that the clinician is to follow to reach the target. One such navigation software is the ILOGIC® navigation suite currently sold by Medtronic PLC.

Once catheter 12 has been successfully navigated proximate the target as depicted on the user interface, the locatable guide 32 may be unlocked from catheter 12 and removed, leaving catheter 12 in place as a guide channel for guiding medical instruments. Such medical instruments may include, without limitation, optical systems, ultrasound probes, marker placement tools, biopsy tools, ablation tools (i.e., microwave ablation devices), laser probes, cryogenic probes, sensor probes, and aspirating needles.

The three-dimensional model of a patient's lungs, generated from previously acquired CT scans, may not provide a basis sufficient for accurate guiding of the catheter 12 of the catheter guide assembly 40 to a target during the procedure. As described above, the inaccuracy may be caused by CT-to-Body divergence (deformation of the patient's lungs during the procedure relative to the lungs at the time of the acquisition of the previously acquired CT data). Thus, another imaging modality is necessary to visualize targets and/or a terminal bronchial branch, and enhance the electromagnetic navigation procedure by correcting the navigation during the procedure, enabling visualization of the target, and confirming placement of the medical or surgical device during the procedure. For this purpose, the system described herein processes and converts image data captured by the fluoroscopic imaging device 10 to a 3D reconstruction of the target area as is described herein. This fluoroscopic image data may be utilized to identify such targets and terminal bronchial branches or be incorporated into, and used to update, the data from the CT scans in an effort to provide a more accurate navigation procedure. Further, the fluoroscopic images may be captured post-navigation and thus include visuals of the catheter 12 and any medical devices positioned therethrough relative to the target.

Figure 4:
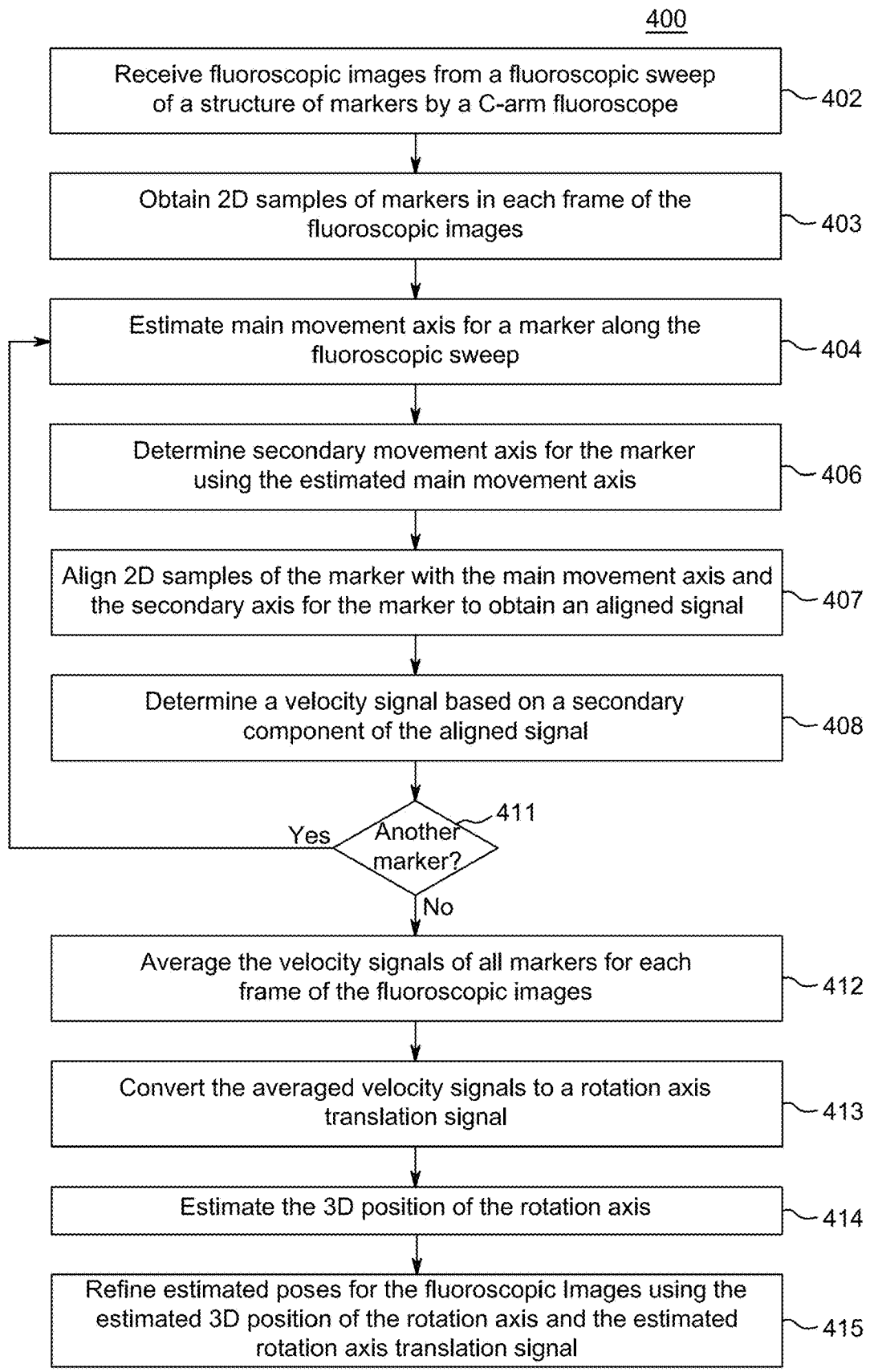
FIG. 4 is a flow chart of a method of compensating for secondary movement of a C-arm fluoroscope in accordance with aspects of this disclosure.
Figure 5:
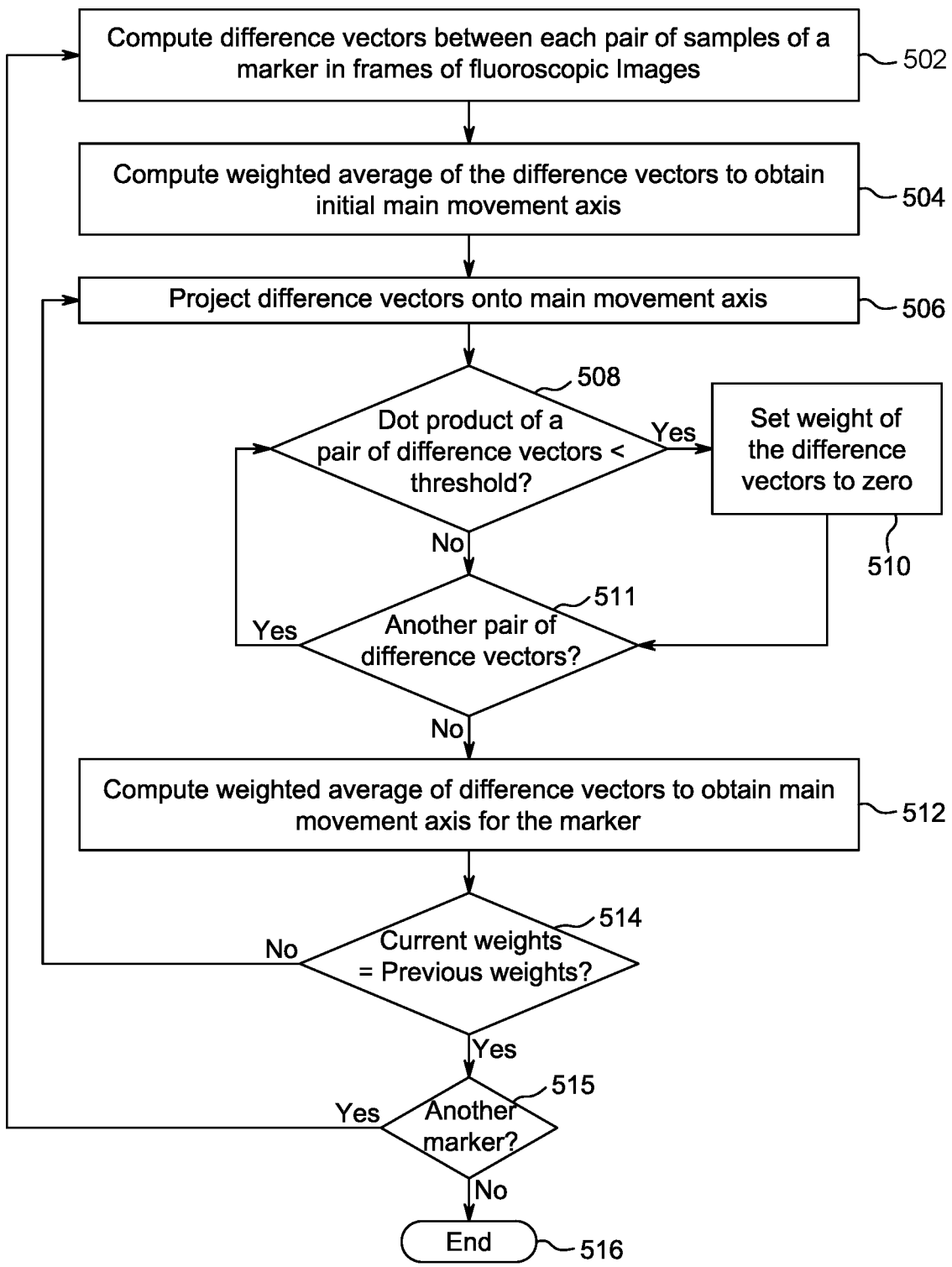
FIG. 5 is a flow chart of a method for estimating a primary movement axis in accordance with aspects of this disclosure.

Reference is now made to FIG. 2A, which is a schematic diagram of a system 200 configured for use with the methods of FIGS. 4 and 5 as described herein. System 200 may include the computing device 25 of FIG. 1 and a fluoroscopic imaging device or C-mount fluoroscope 10 of FIG. 1. In some aspects, workstation 80 may be coupled to the C-mount fluoroscope 10, directly or indirectly, e.g., by wireless communication. Workstation 80 may include memory 202 (e.g., a storage device), a processor 204, a display 206, and an input device 210. Processor 204 may include one or more hardware processors. Workstation 80 may optionally include an output module 212 and a network interface 208.

Memory 202 may store an application 81 and image data 214 including fluoroscopic imaging data. Application 81 may include instructions executable by processor 204 for, among other functions, executing the methods of this disclosure including the methods of FIGS. 4 and 5 described herein. Application 81 may further include a user interface 216. Image data 214 may include the 3D imaging data such as a pre-operative CT scan, the fluoroscopic three-dimensional reconstructions (F3DRs) of the target area, and/or any other fluoroscopic image data and/or one or more virtual fluoroscopy images. Processor 204 may be coupled with memory 202, display 206, input device 210, output module 212, network interface 208, and fluoroscopic imaging device 215. Workstation 80 may be a stationary computing device, such as a personal computer, or a portable computing device such as a tablet computer. Workstation 80 may embed multiple computer devices.

Memory 202 may include any non-transitory computer-readable storage media for storing data and/or software including instructions that are executable by processor 204 and which control the operation of workstation 80 and in some aspects, may also control the operation of fluoroscopic imaging device 215. Fluoroscopic imaging device 215 is used to capture a sequence of fluoroscopic images based on which the F3DR is generated. The two-dimensional fluoroscopic images in which the medical device is selected may be selected from the captured sequence of fluoroscopic images. In an aspect, storage device or memory 202 may include one or more storage devices such as solid-state storage devices such as flash memory chips. Alternatively, or in addition to the one or more solid-state storage devices, memory 202 may include one or more mass storage devices connected to the processor 204 through a mass storage controller (not shown) and a communications bus (not shown).

Although the description of computer-readable media contained herein refers to a solid-state storage, it should be appreciated by those skilled in the art that computer-readable storage media can be any available media that can be accessed by the processor 204. That is, computer readable storage media may include non-transitory, volatile and non-volatile, removable and non-removable media implemented in any method or technology for storage of information such as computer-readable instructions, data structures, program modules or other data. For example, computer-readable storage media may include RAM, ROM, EPROM, EEPROM, flash memory or other solid-state memory technology, CD-ROM, DVD, Blu-Ray or other optical storage, magnetic cassettes, magnetic tape, magnetic disk storage or other magnetic storage devices, or any other medium which may be used to store the desired information, and which may be accessed by workstation 80.

Application 81 may, when executed by processor 204, cause display 206 to present user interface 216. User interface 216 may be configured to present to the user the F3DR, two-dimensional fluoroscopic images, images of the 3D imaging, and a virtual fluoroscopy view. User interface 216 may be further configured to direct the user to select the target by, among other things, identifying and marking the target in the displayed F3DR or any other fluoroscopic image data in accordance with this disclosure.

Network interface 208 may be configured to connect to a network such as a local area network (LAN) consisting of a wired network and/or a wireless network, a wide area network (WAN), a wireless mobile network, a Bluetooth network, and/or the internet. Network interface 208 may be used to connect between workstation 80 and fluoroscopic imaging device 215. Network interface 208 may be also used to receive image data 214. Input device 210 may be any device by means of which a user may interact with workstation 80, such as, for example, a mouse, keyboard, foot pedal, touch screen, and/or voice interface. Output module 212 may include any connectivity port or bus, such as, for example, parallel ports, serial ports, universal serial busses (USB), or any other similar connectivity port known to those skilled in the art.

Figure 3:
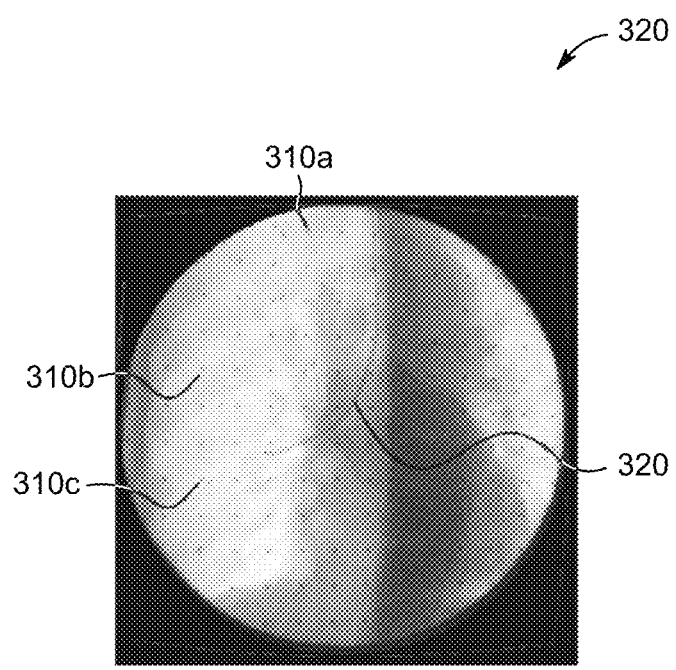
FIG. 3 is an exemplary image captured by a fluoroscopic device of an artificial chest volume of a Multipurpose Chest Phantom N1 "LUNGMAN", by Kyoto Kagaku, placed over the grid structure of radio-opaque markers of FIG. 2B.

Reference is now made to FIGS. 2B and 3. FIG. 2B is a schematic illustration of a two dimensional (2D) grid structure of sphere markers 220 in accordance with the disclosure. FIG. 3 is an exemplary image 300 captured by a fluoroscopic device of an artificial chest volume of a Multipurpose Chest Phantom N1 "LUNGMAN", by Kyoto Kagaku, placed over the 2D grid structure of sphere markers 220 of FIG. 2B. The 2D grid structure of sphere markers 220 includes sphere-shaped markers, such as sphere markers 230a and 230b, arranged in a two dimensional grid pattern. Image 300 includes a projection of a portion of 2D grid structure of sphere markers 220 and a projection of a catheter 320. The projection of 2D grid structure of sphere markers 220 on image 300 includes projections of the sphere markers, such as sphere marker projections 310a, 310b, and 310c.

Each of the markers of the structure of markers may take any form suitable for identifying and tracking the markers in the fluoroscopic images. For example, the markers may be in the shape of squares, circles, dots, or other suitable symbols or shapes. In one aspect, the markers may be radiopaque beads.

Aspects of this disclosure use fluoroscopic images of the structure of markers from a fluoroscopic sweep by a C-arm fluoroscope to detect wigwag movement and to compensate for the wigwag movement by making refinements to the camera of the C-arm fluoroscope or to the fluoroscopic images from the camera of the C-arm fluoroscope. The wigwag movement includes C-arm movement which is approximately perpendicular to the rotation or sweep movement of the C-arm.

Aspects of this disclosure estimate the C-arm movement component that is not the sweep movement. This is mainly a movement along the rotation axis caused by an untightened wigwag lock as described above. In aspects, this disclosure uses the intersection point between the rotation axis and the C-arm plane as a 3D reference point. The three-dimensional (3D) movement of the C-arm is estimated along the rotation axis by examining the two-dimensional (2D) movement of a structure of markers (e.g., a fiducial grid) in the fluoroscopy video of the C-arm fluoroscope. The 2D movement of the structure of markers is broken down into main and secondary movement axes. The 2D movement along the secondary axis is converted to an amplitude of the 3D reference point by performing geometrical computations.

The 3D axis along which the reference point moves is estimated by reconstructing the C-arm plane, which is a plane on which the source and detector reside along the fluoroscopic sweep, and determining the axis normal to the C-arm plane. A 2D estimate for the projection of the 3D reference point is obtained by: computing, for each frame of fluoroscopic images from the fluoroscopic sweep, the 3D reference point based on the model specifications of the C-arm fluoroscope and initial movement estimates of the source or camera of the C-arm fluoroscope; averaging the 3D reference points estimated from all fluoroscopic frames; projecting the averaged 3D reference point on each fluoroscopic image frame; and averaging the 2D projection coordinates. The result is a single 2D coordinate onto which the rotation axis reference point projects. Then, the camera is refined based on the 2D and 3D coordinates of the structure of markers and rotation axis reference point.

FIG. 4 shows a flow chart of a method 400 of compensating for wigwag movement in a fluoroscopic sweep according to an aspect of this disclosure. At block 402, fluoroscopic images from a fluoroscopic sweep of the structure of markers are received. At block 403, 2D samples of markers are obtained in each frame of the fluoroscopic images. Obtaining 2D samples of the markers may include detecting markers of a structure of 2D markers in each of the fluoroscopic images and determining the position of each of the detected markers in each of the fluoroscopic images. Each of the markers in each of the fluoroscopic images may be detected using a suitable marker recognition process.

Figure 6A:
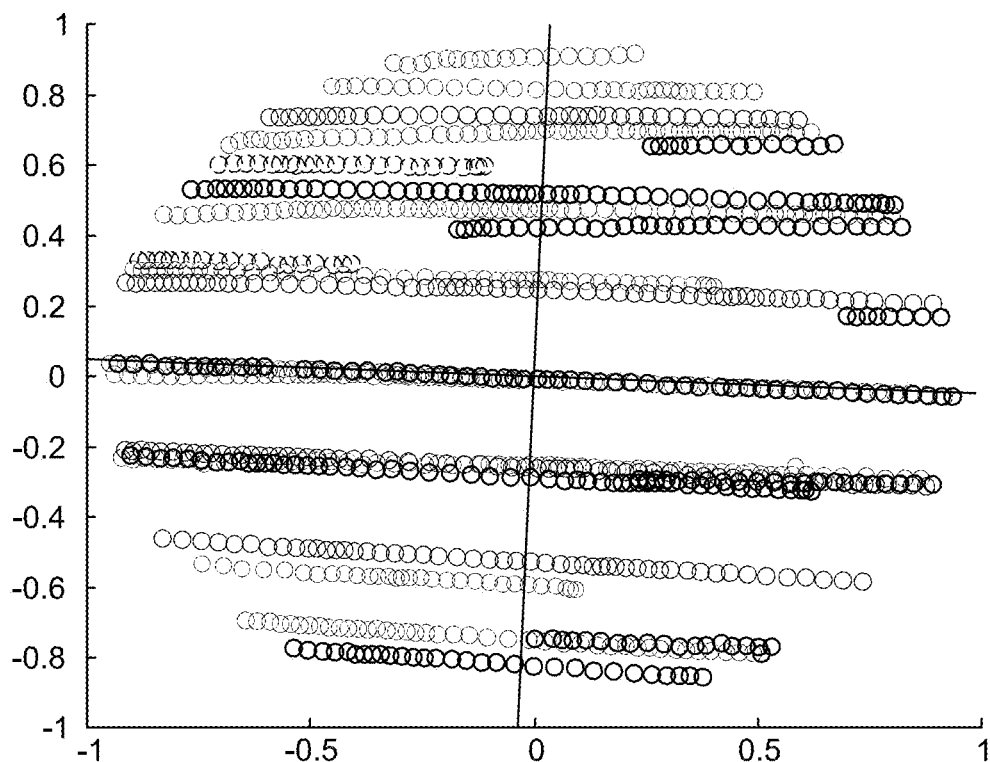
FIG. 6A is a graphical diagram of marker samples from an example of a fluoroscopic sweep without wigwag movement.
Figure 6B:
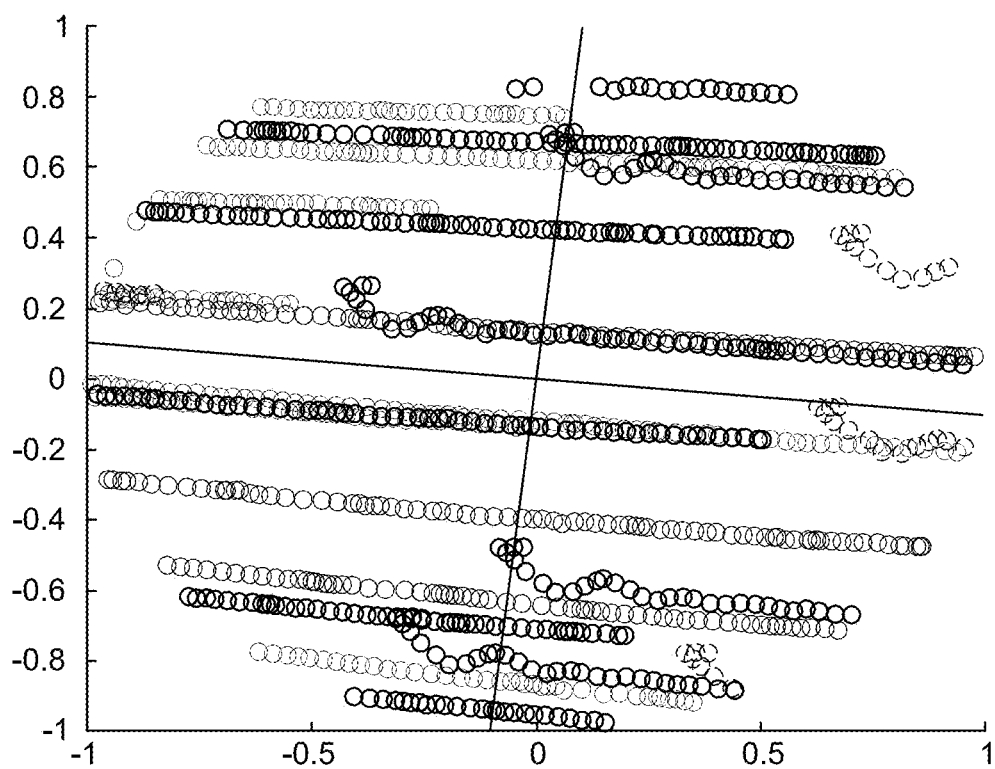
FIG. 6B is a graphical diagram of marker samples from an example of a fluoroscopic sweep with wigwag movement.

At block 404, the main movement axis for each marker of the structure of markers is estimated along a fluoroscopic sweep. In one aspect, the difference vectors between each pair of samples of a marker in frames of fluoroscopic images is computed at block 502. FIGS. 6A and 6B show examples of first samples of markers 601 from fluoroscopic images of a fluoroscopic sweep using a C-arm fluoroscope without wigwag movement and second samples of markers 602 from fluoroscopic images of a fluoroscopic sweep using a C-arm fluoroscope with wigwag movement. The difference vectors may be normalized, and the norms or distances associated with the difference vectors may be used as weights to compute the weighted average at block 504. At block 504, the initial main movement axis for a marker is computed at block 504 by computing the weighted average of the difference vectors based on the norm of each of the difference vectors or the distance between each pair of samples of the marker. The weighted main movement axis is then iteratively computed. At block 506, each individual difference vector is projected onto the initial or current main movement axis. This may be accomplished by determining the dot product between pairs of difference vectors.

At block 508, the method 500 determines whether the dot product of pairs of difference vectors is less than a threshold. For a pair of difference vectors with a dot product less than the certain threshold, their corresponding weights are set to zero at block 510 in the case where binary weights are used. In other aspects, non-binary weights may be used. At block 511, the method 500 determines whether there is another pair of difference vectors to process. If there is another pair of difference vectors that has not yet been processed, the method 500 repeats block 508 and/or block 510 for the other pair of difference vectors. If there is not another pair of difference vectors to process because all pairs of difference vectors have been processed according to block 508 and/or block 510, the method 500 proceeds to block 512.

At block 512, the initial or current main movement axis is recomputed by taking a weighted average of the difference vectors. At block 514, the method 500 determines whether the current weights are equal to the previous weights. If the reweighting process does not change the weights from a previous iteration, the reweighting process is stopped and the method 500 proceeds to block 515. Otherwise, the method 500 iteratively repeats blocks 506-514 until there is no change in weights between iterations. At block 515, the method 500 determines whether there is another marker to process. If there is another marker that has not yet been processed, the method 500 repeats blocks 502-514 for the other marker. If there is not another marker to process because all markers have been processed according to blocks 502-514, the method 500 ends at block 516.

At block 406, the secondary movement axis, which is orthogonal or perpendicular to the main movement axis, is determined for each marker using the estimated main movement axis. The secondary movement axis may be determined by processing the estimated main movement axis with a Graham-Schmidt algorithm.

Figure 7A:
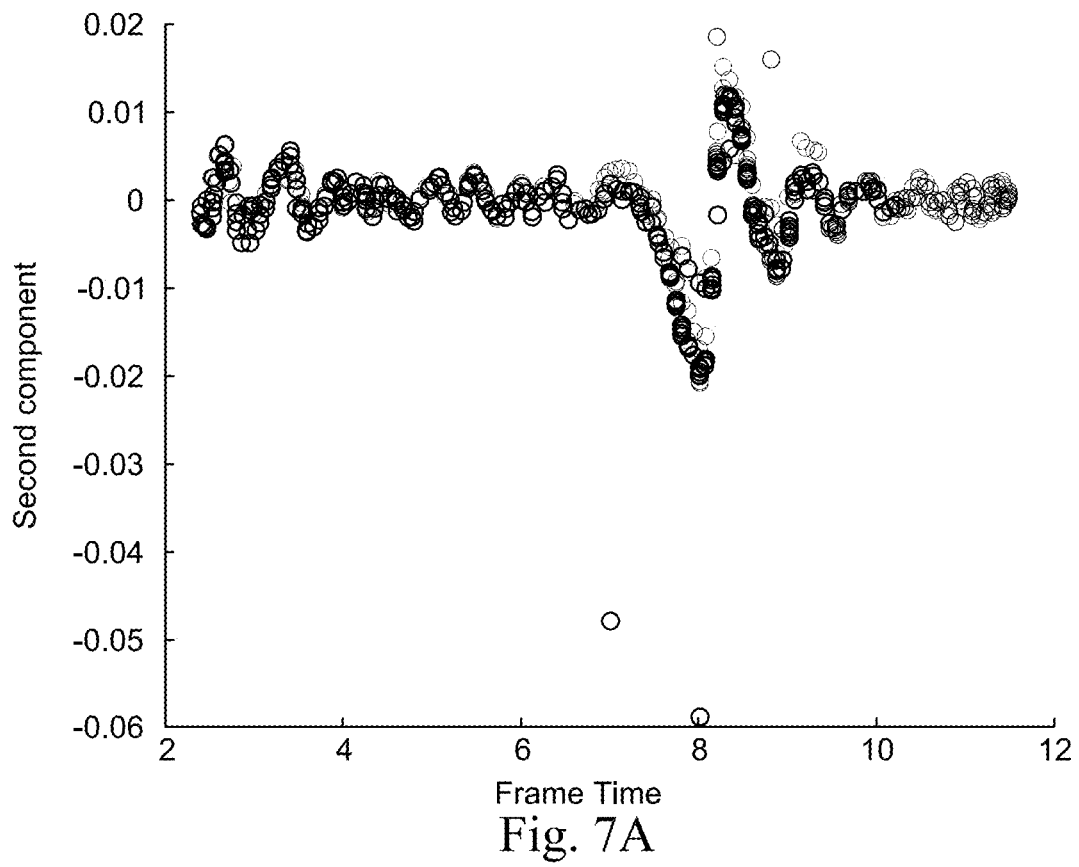
FIG. 7A is a graphical diagram of velocity values of a secondary component of marker samples from an example of a fluoroscopic sweep.

At block 407, the two-dimensional (2D) samples of a marker are aligned with the main movement axis and the secondary movement axis for the marker to obtain an aligned signal. At block 408, a position difference signal is determined based on the secondary component of the aligned signal. For each marker, the position difference signal is collected as a function of time or a frame index. Since the 2D samples of the marker are sampled at constant time differences, the position difference signal may be referred to as a speed or velocity signal. FIG. 7A shows an example of velocity signal values of a secondary component of the aligned signal as a function of frame time.

Figure 8:
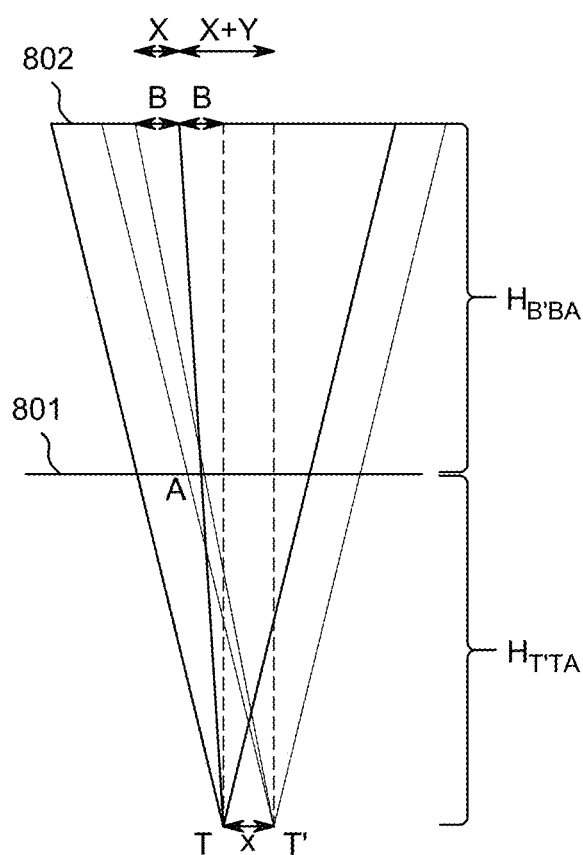
FIGS. 8 and 9 are schematic diagrams of representations of the C-arm and structure of markers geometry.

The velocity signal of each marker is in the image space. Thus, using geometry, a velocity signal for a marker can be converted to the equivalent movement of the C-arm in a direction perpendicular to the movement of the main rotation axis based on a 3D coordinate of a marker as illustrated in FIG. 8. Accordingly, the velocity signal is converted to a rotation axis signal. As shown in FIG. 8, the X-ray source T and the rotation axis move simultaneously. Thus, movement in the detector plane 802 is converted into movement of the X-ray source T, which is equal to the movement of the rotation axis.

Since wigwag movement is parallel to the detector plane 802, the movement of the X-ray source T can be estimated using triangle similarity between triangle B'BA and triangle T'TA, where A is a position at which the line BT intersects with the marker plane 801. As shown in FIG. 8, the bases ratio is equal to the height ratio. In addition, the detector also shifts together with the X-ray source T. Therefore, movement of the X-ray source T may be solved in the following way.

Figure 9:
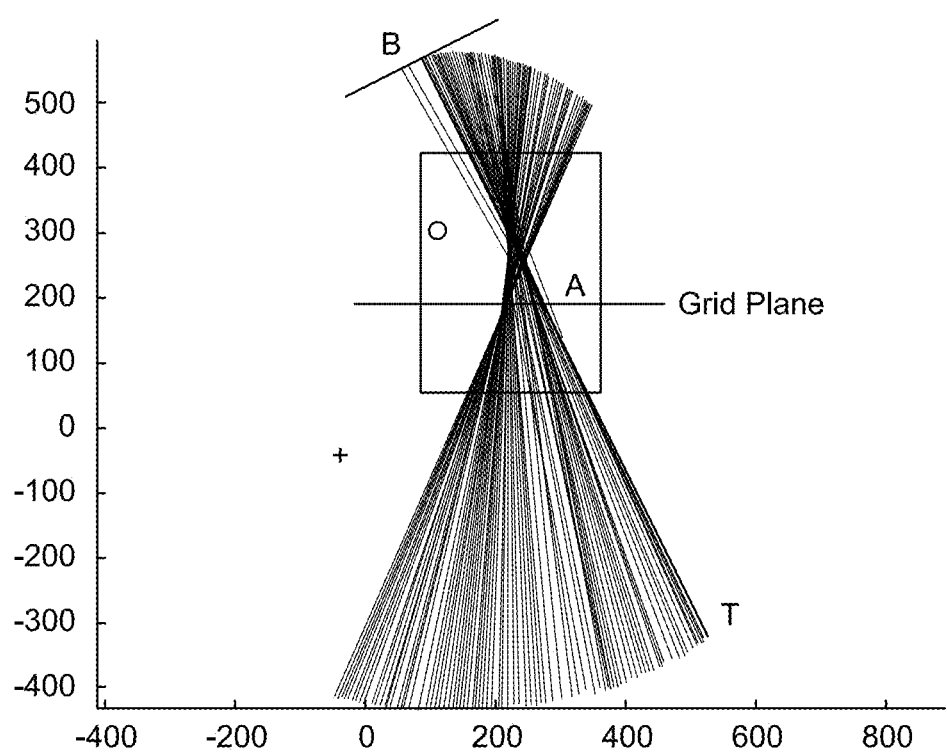

The similarity ratio may be computed according to the following expression: $R=H_{T'TA}/H_{B'BA}$, where $H_{T'TA}$ is the height of triangle T'TA and $H_{B'BA}$ is the height of triangle B'BA. The heights of triangles B'BA and T'TA may be computed in the following way. Assuming that B is the center of the image, A is the intersection of the z axis of the X-ray source with the plane y=0. As shown in FIG. 9, the B'B/T'T ratio is equal to the height ratio. Thus, only AT/AB needs to be computed. Accordingly, T'T=B'B×AT/AB.

Using the similarity ratio R, the distance B'B is calculated according to the expression: B'B=Rx+x, where x is the movement of the X-ray source T. Solving for the X-ray source movement x, leads to the following expression for calculating the X-ray source movement: x=B'B/(R+1).

Next, for each frame, the 3D position of the point of intersection between the rotation axis and the C-arm fluoroscope plane is estimated in the following way. The sign of the estimated wigwag movement B'B in the detector plane is determined. Then, the current shift is calculated according to the following expression: Current shift=X-ray source movement×Sign(B'B)×ax1, where Sign(x) is a function that outputs the sign of x, and ax1 represents the primary components of the sweep, which may be obtained by averaging the primary components of the sweep for all the markers. To calculate the current rotation axis position, the current shift is added to the initial estimation of the rotation axis position, which assumes a static axis and no wigwag movements. The addition takes place in the XZ plane since the rotation axis movement is on the plane parallel to the marker plane 801.

At block 411, the method 400 includes determining whether there is another marker to process. If there is another marker to process, the method 400 includes performing blocks 404-408 for another marker. If there is not another marker to process, the method 400 proceeds to block 412.

Figure 7B:
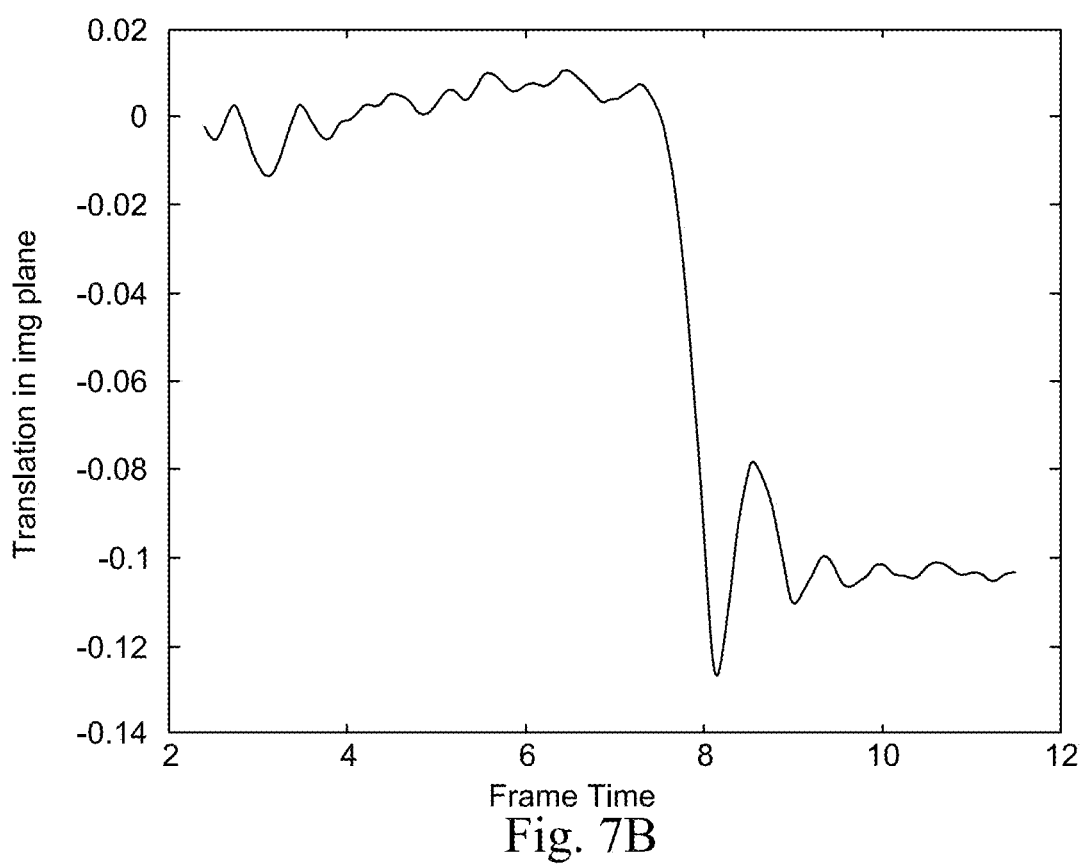
FIG. 7B is a graphical diagram of translation values estimated from the velocity values of FIG. 7A.
Figure 7C:
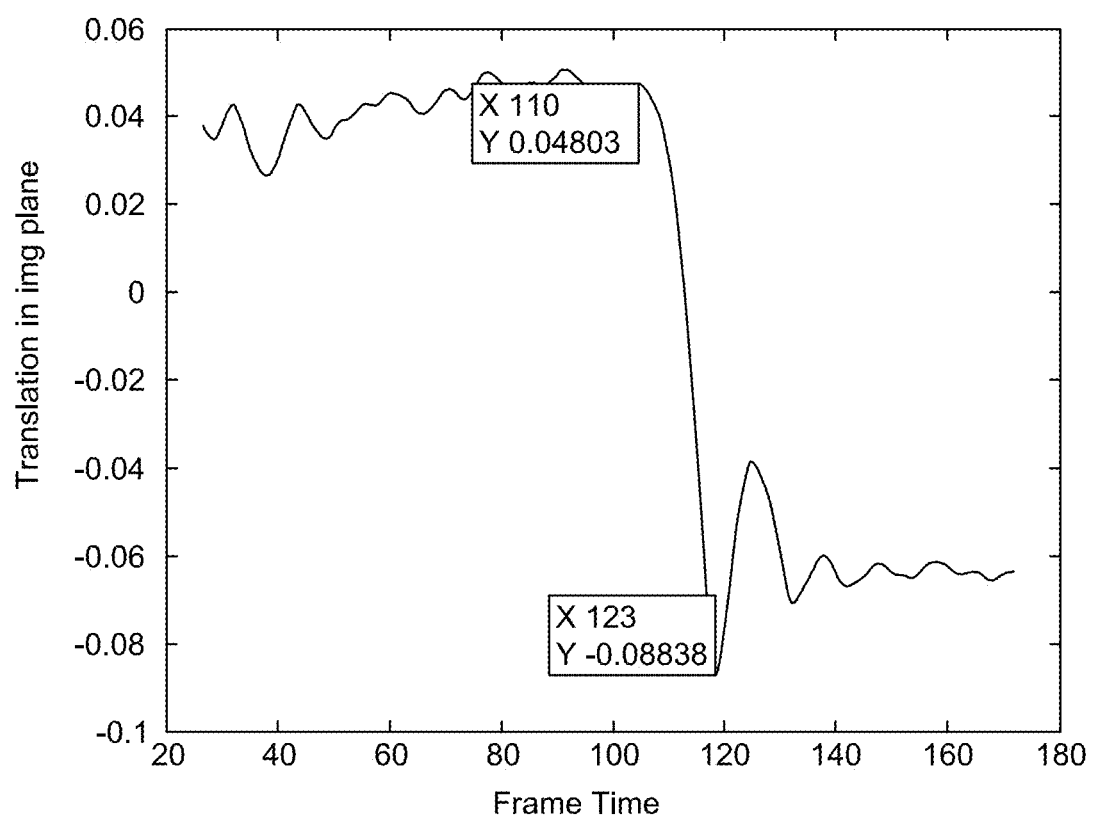
FIG. 7C is a graphical diagram of the translation values of FIG. 7B shifted by a mean value.

To estimate the wigwag amplitude for each frame of the fluoroscopic images from the fluoroscopic sweep, the velocity signal values of all markers at each frame index of the fluoroscopic images are averaged at block 412. The averaged velocity signal values may be agglomerated to the last position. Also, the position at the first frame of the fluoroscopic images from the fluoroscopic sweep may be set to zero. At block 413, the averaged velocity signals are converted to an estimated rotation axis translation signal using geometrical relationships between the image plane and the 3D position of the rotation axis. The rotation axis translation signal may be estimated by integrating the averaged velocity signals to obtain a translation signal and shifting the translation signal by the average value of the translation signal. The shifted translation signal represents an amplitude or the size of the translation along the estimated rotation axis in 3D at each frame or time stamp. FIG. 7B shows an example of an estimated rotation axis translation signal generated based on the velocity signal values of FIG. 7A. FIG. 7C shows an example of the estimated rotation axis translation signal of FIG. 7B shifted by the average value of the translation signal.

At block 414, the 3D position of the rotation axis is estimated. As described above, the rotation axis is perpendicular to the direction of the fluoroscope sweep. Thus, to estimate the 3D position of the rotation axis, a plane that contains the z-axis of all X-ray source positions (as illustrated in FIG. 9) is fit along the sweep and the axis normal to this plane is determined as the rotation axis. At block 415, the estimated poses for the fluoroscopic images are refined using the estimated 3D position of the rotation axis and the estimated rotation axis translation signal.

From the foregoing and with reference to the various figure drawings, those skilled in the art will appreciate that certain modifications can also be made to this disclosure without departing from the scope of the same. For example, although the systems and methods are described as usable with an EMN system for navigation through a luminal network such as the lungs, the systems and methods described herein may be utilized with systems that utilize other navigation and treatment devices such as percutaneous devices. Additionally, although the above-described system and method is described as used within a patient's luminal network, it is appreciated that the above-described systems and methods may be utilized in other target regions such as the liver.

Detailed aspects are disclosed herein. However, the disclosed aspects are merely examples of the disclosure, which may be embodied in various forms and aspects. Therefore, specific structural and functional details disclosed herein are not to be interpreted as limiting, but merely as a basis for the claims and as a representative basis for teaching one skilled in the art to variously employ this disclosure in virtually any appropriately detailed structure.

As can be appreciated a medical instrument such as a biopsy tool or an energy device, such as a microwave ablation catheter, that is positionable through one or more branched luminal networks of a patient to treat tissue may prove useful in the surgical arena and this disclosure is directed to systems and methods that are usable with such instruments and tools. Access to luminal networks may be percutaneous or through a natural orifice using navigation techniques. Additionally, navigation through a luminal network may be accomplished using image-guidance systems. The image-guidance systems may be separate or integrated with the energy device or a separate access tool and may include MRI, CT, fluoroscopy, ultrasound, electrical impedance tomography, optical, and/or device tracking systems.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

While several aspects of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular aspects. Those skilled in the art will envision other modifications within the scope and spirit of the claims appended hereto.

What is claimed is:

1. A method of compensating for secondary movement of a C-arm fluoroscope, the method comprising:
receiving fluoroscopic images obtained from a fluoroscopic sweep by the C-arm fluoroscope;
detecting markers of a structure of two-dimensional (2D) markers in the fluoroscopic images to obtain detected markers;
determining movement of the markers based on the detected markers;
estimating a primary movement axis based on the movement of the markers;
determining a secondary movement axis based on the primary movement axis;
estimating a translation of the markers in a direction of the secondary movement axis;
estimating a rotation axis translation based the translation of the markers;
estimating a three-dimensional (3D) position of a rotation axis;
estimating poses for the fluoroscopic images; and
refining the poses for the fluoroscopic images based on the rotation axis translation and the 3D position of the rotation axis.

2. The method of claim 1, wherein each marker of the structure of 2D markers is a radiopaque bead or a radiopaque marker.

3. The method of claim 1, wherein the structure is a 2D grid pattern.

4. The method of claim 1, wherein estimating the translation of the markers includes:

aligning each marker with the primary movement axis and the secondary movement axis to obtain an aligned signal; and determining a difference signal of each marker for a secondary component of the aligned signal.

5. The method of claim 1, wherein the secondary movement axis is determined by processing the primary movement axis with a Graham-Schmidt algorithm.

6. The method of claim 1, wherein estimating the 3D position of the rotation axis includes:

fitting a plane to main camera axes of the C-arm fluoroscope over the fluoroscopic sweep; and computing an axis normal to the plane to obtain the 3D position of the rotation axis.

7. The method of claim 1, wherein estimating the primary movement axis of the markers includes:

determining, for each of the markers, difference vectors between pairs of detected markers in adjacent pairs of frames of the fluoroscopic images; and computing, for each pair of frames, a weighted average of the difference vectors, wherein weights applied to the difference vectors are distances between the pairs of detected markers.

8. The method of claim 7, wherein estimating the primary movement axis of the markers further includes:

computing a dot product between difference vectors;

determining that the dot product is less than a threshold;

in response to determining that the dot product is less than the threshold, setting the weights of the difference vectors to zero;

recomputing, for each pair of frames, a weighted average of the difference vectors;

determining that weights of a current iteration are the same as weights of a previous iteration; and in response to determining that the weights of a current iteration are the same as the weights of a previous iteration, stopping computing of the weighted average.

9. A method for estimating wigwag movement in a C-arm fluoroscope, the method comprising:

receiving fluoroscopic images of a structure of markers from a sweep of the C-arm fluoroscope;

obtaining two-dimensional (2D) samples of each marker of the structure of markers from the fluoroscopic images;

estimating a main movement axis of each marker based on the 2D samples of each marker;

determining a secondary movement axis of each marker based on the main movement axis of each marker;

aligning 2D samples of each marker with the main movement axis and the secondary movement axis for each marker to obtain an aligned signal of each marker;

determining a velocity signal of each marker for a secondary component of the aligned signal of each marker;

converting the velocity signals of the markers to a rotation axis translation signal; and estimating a rotation axis for the rotation axis translation signal.

10. The method of claim 9, wherein each marker is part of a structure of markers.

11. The method of claim 9, wherein the structure is a 2D grid pattern.

12. The method of claim 9, wherein estimating the rotation axis includes:

fitting a plane to main camera axes of the C-arm fluoroscope over the sweep; and computing a normal axis to the plane to obtain the rotation axis.

13. The method of claim 9, wherein estimating the main movement axis of each marker of the structure of markers includes:

determining, for each marker of the structure of markers, difference vectors between pairs of markers in adjacent pairs of frames of the fluoroscopic images; and computing, for each pair of frames, a weighted average of the difference vectors, wherein the weights applied to the difference vectors are distances between the pairs of markers.

14. The method of claim 9, wherein the secondary movement axis is determined by processing the main movement axis of each marker of the structure of markers with a Graham-Schmidt algorithm.

15. The method of claim 9, wherein converting the velocity signal of each marker to a rotation axis velocity signal includes:

determining a similarity ratio for each marker; and applying the similarity ratio to each marker to obtain the rotation axis velocity signal.

16. The method of claim 9, wherein converting the velocity signals of the markers to a rotation axis translation signal includes:

averaging the velocity signals for all markers for each of the fluoroscopic images to obtain an averaged velocity signal; and converting the averaged velocity signal to the rotation axis translation signal.

17. The method of claim 16, wherein converting the averaged velocity signal to the rotation axis translation signal includes integrating the averaged velocity signal across all fluoroscopic images to obtain the rotation axis translation signal.

18. The method of claim 16, further comprising estimating a pose for each of the fluoroscopic images based on the 2D samples of the markers, the rotation axis translation signal, and the rotation axis.

19. The method of claim 18, wherein the markers are a grid of radiopaque beads.

* * * * *